United States Patent [19]

Voorhees et al.

[11] 4,190,669

[45] Feb. 26, 1980

[54] METHOD FOR TREATING PSORIASIS

[75] Inventors: John J. Voorhees, Ann Arbor, Mich.;
Sven R. Hammarström, Djursholm,
Sweden; Mats A. Hamberg, Lidingö,
Sweden; Bengt I. Samuelsson,
Danderyd, Sweden

[73] Assignee: The Regents of the University of Michigan, Ann Arbor, Mich.

[21] Appl. No.: 793,099

[22] Filed: May 2, 1977

Related U.S. Application Data

[63] Continuation-in-part of Ser. No. 664,652, Mar. 8, 1976, abandoned.

[51] Int. Cl.$^2$ .................. A61K 31/215; A61K 31/185
[52] U.S. Cl. ..................................... 424/305; 424/14;
424/239; 424/315; 424/317; 424/318; 424/361;
424/362
[58] Field of Search ................ 424/305, 317, 318, 315

[56] References Cited
U.S. PATENT DOCUMENTS

| | | | |
|---|---|---|---|
| 3,033,884 | 5/1962 | Osbond et al. ................... | 260/413 L |
| 3,450,821 | 6/1969 | Cartensen et al. ................. | 424/318 |
| 3,903,297 | 9/1975 | Robert .................................. | 424/318 |

OTHER PUBLICATIONS

Solomon et al., The Journal of Investigative Dermatology, 1968, vol. 51, No. 4.
Strauss et al., Chem. Abs., 1967, vol. 67, p. 2042x.

*Primary Examiner*—Dale R. Ore
*Attorney, Agent, or Firm*—Neal A. Waldrop

[57] ABSTRACT

A process for the treatment of psoriasis comprising administering to humans or domesticated animals topically and/or systemically a composition comprising a pharmaceutical carrier and eicosa-5,8,11,14-tetraynoic acid, its congeners, and the lower alkyl esters thereof; in one preferred form of the invention the composition comprises a pharmaceutical carrier and 5,8,11 eicosatriynoic acid; in another preferred form of the invention the composition comprises a pharmaceutical carrier and at least one active compound selected from the groups eicosa-5,8,11,14-tetraynoic acid, its congeners and the lower alkyl esters thereof and at least one compound selected from the group consisting of $PGE_1$, $PGE_2$, $PGE_3$ and the alkyl esters thereof containing from 1 to 8 carbon atoms inclusive, and 13,14-dihydro $PGE_1$ and the alkyl esters thereof containing from 1 to 8 carbon atoms inclusive.

11 Claims, No Drawings

METHOD FOR TREATING PSORIASIS

CROSS REFERENCE TO RELATED APPLICATIONS

This application is a continuation in part of copending application Ser. No. 664,652, filed Mar. 8, 1976 now abandoned.

BRIEF DESCRIPTION OF THE INVENTION

This invention relates to pharmaceutical compositions for and a method of treating psoriasis. The compositions may be applied topically or by injection such that the composition enters the blood stream, or intralesionally or intradermally or subcutaneously or orally. The treatment may be either therapeutic or prophylactic.

DETAILED DESCRIPTION OF THE INVENTION

Psoriasis is well-known to afflict two to three percent of the earth's population and is considered by most to be one of man's most unsightly, painful, morbid diseases. Psoriasis is a complex disorder of many varieties and is not completely medically understood even though extensive research and effort has been expended in the attempt to determine and identify its cause and to provide a cure. It is known that the epidermis of a psoriasis patient is characterized by excessive cell proliferation, incomplete terminal differentiation and glycogen accumulation. Although many compositions and methods for alleviating psoriasis have been proposed and used, only certain of them have been successful; even those considered successful usually alleviated the disease only for temporary periods. There is still a need for improved compositions and methods for treating psoriasis.

Previously existent compositions and treatments for psoriasis have provided in certain cases some remission of the original symptoms, or a temporary cure, but each composition or treatment heretofore known suffers from some defect to some degree. For a treatment to constitute a cure for psoriasis, it must be both safe and effective to cause an enduring remission of all the psoriasis lesions on the body to a degree such that they disappear and the skin assumes a normal appearance and is healthy and functional on a continuing basis. Alleviation of psoriasis to a degree less than a complete cure is useful and desirable because a treatment which accomplishes an alleviation in a seriously afflicted patient may be satisfactory to effect a substantially complete or permanent cure in a less seriously afflicted patient.

The primary object of this invention is to provide a pharmaceutical composition for and a method of treating psoriasis. One of the specific objectives of the invention is to provide a pharmaceutical composition for administration to psoriasis patients which is safe and capable of alleviating psoriasis in a short period of time, or curing same. In accordance with this invention it has been found that psoriasis is alleviated, that is, the symptoms of the disease are noticeably improved or become undetectable by the treatment of the afflicted patient or animal with one or more of the pharmaceutical compositions described in detail hereinbelow. For purposes of this invention and as claimed herein, psoriasis is alleviated when a scale-free psoriasis lesion is noticeably decreased in thickness, or noticeably but incompletely cleared, or completely cleared; indications of such alleviation include restoration of cell proliferation rate, and/or terminal differentiation, and/or glycogen content to near normal levels.

U.S. Pat. No. 3,033,884 discloses unsaturated aliphatic compounds having the general formula

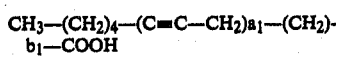

and the alkyl esters of such compounds. This disclosure describes the method of manufacture of such compounds and indicates that they are unsaturated acids which may be useful in replacing, or substituting for essential fatty acids in humans or animals by addition to foods and feedstuffs and can also be used in the therapy of pathologic, inflammatory or scaly skin disorders and for the treatment of arteriosclerosis.

U.S. Pat. No. 3,045,821 describes therapeutic compositions, including eicosatetrayn-(5,8,11,14)-oic-(1) acid in admixture with a material selected from the group consisting of edible oils, edible waxes or mixtures thereof as compositions which will not deteriorate or decompose after long periods of standing or storage. The specification refers to the earlier disclosure of U.S. Pat. No. 3,033,884 relative to the general statement of potential or possible uses as above indicated.

An article by Sven Hammarstrom, Mats Hamberg, Bengt Samuelsson, Elizabeth A. Duell, Marek Stawiski, and John J. Voorhees in the "Proceedings to the National Academy of Science" U.S.A., Vol. 72, No. 12, pp. 5130–5134, published in December of 1975, discloses the effect of the level of prostaglandins, in vitro, in tests removed from humans having psoriasis caused by the addition of small quantities of 5,8,11,14-eicosatetraynoic acid at p. 5132 and the effect on the level of HETE, 12L-hydroxy-5, 8, 10,14-eicosatetraenoic acid at p. 5133.

The compositions of this invention may be applied topically or by injection such that the composition enters the blood stream, or intradermally, intra- or peri-lesionally, or subcutaneously.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compounds is applied externally by direct contact with the skin surface to be treated. Conventional pharmaceutical forms for this purpose include ointments, lotions, pastes, jellies, sprays, aerosols, bath oils and the like. The term "ointment" embraces formulations (includng creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

Certain of the compositions of this invention advantageously include skin penetrating adjuvants such as, for example, dimethyl sulfoxide, dimethyl acetamide, etc.

Injection "intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected so as to reach the blood stream intramuscularly, subcutaneously, rectally by suppositories, sublingually, intravenously, orally, by inhalation, or by application to non-diseased skin.

The best mode of practicing the process of this invention is to treat the afflicted animal, or human, so as to cause a continuing release of the active compound at the afflicted site or sites, at a selected, controlled rate which is sustained for an extended time period.

The compositions of this invention comprise a pharmaceutical carrier and about 0.1% to about 15%, w/v, of at least one of the compounds have the formula

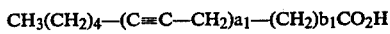

$$CH_3(CH_2)_4-(C\equiv C-CH_2)_{a_1}-(CH_2)_{b_1}CO_2H$$

wherein $a_1$ stands for an integer of from 3 to 5 and $b_1$ stands for an integer of from 0 to 8, and the alkyl esters of such compounds.

A preferred subgroup of compounds encompassed by the above formula are those wherein $a_1$ is 3 and 4 and $b_1$ is 5 when $a_1$ is 3 and $b_1$ is 2 when $a_1$ is 4.

Preferred compounds are eicosatetrayn-(5,8,11,14)-oic-(1) acid and its alkyl esters.

Other compounds suitable for the formulations of this invention include $$CH_3(CH_2)_m(C\equiv C-CH_2)_a(CH_2)_bCO_2H$$ and its alkyl esters wherein m is an integer from 5 to 9 inclusive, a is an integer of 2 to 5 and b is an integer of from 0 to 8. These compounds may be prepared by methods obvious to one skilled in the art, for example, by substitution of appropriate starting materials in the procedures described in U.S. Pat. No. 3,033,884.

Preferred compounds are 5,8,11-eicosatriynoic acid and its alkyl esters which are capable of producing, in certain cases, a higher level of alleviation of psoriasis than is obtained from the use of eicosatetrayn-(5,8,11,14)-oic-(1) acid.

The amount of the active compound to be used in the compositions of this invention for administration topically, parenterally or systemically ranges from about 0.1% to about 15% w/v topically; from about 0.1% to about 10% w/v parenterally and for oral dosage form of eicosatetrayn-(5,8,11,14)-oic-(1) acid or its esters or pharmaceutically acceptable salts, the amount may range from about 0.1 gram per day to about 5 grams per day, together with the associated carrier and depending upon the needs and requirements of the patient as diagnosed by the attending physician.

The compositions of the present invention are presented for systemic administration to humans and animals in unit dosage forms, such as tablets, capsules, pills, powders, granules, sterile parenteral solutions or suspensions, and oral solutions or suspensions, and oil-water emulsions containing suitable quantities of one or more of the active compounds above described.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical filuents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the active compound or compounds with an inert pharmaceutical diluent and filling the mixture into a hard gelatin capsule or appropriate size. In another embodiment, capsules are prepared by filling hard gelatin capsules with polymeric acid coated beads containing the active compound or compounds. Soft gelatin capsules are prepared by machine encapsulation of a slurry of the active compound or compounds with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacanth, methylcellulose and the like.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

For parenteral administration the dosage forms are prepared utilizing the active compound or compounds and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

For parenteral or systemic administration of the compositions of this invention, the usual dosage of the selected active compound, or compounds, should be employed.

The compositions of this invention may include one or more of the above identified active compounds in a single composition or the method of the invention may be practiced by the administration of a plurality of compositions, each of which contains a single or a plurality of active compounds. In certain cases, the method of the invention may involve the administration of compositions containing a single active compound or a mixture of active compounds by a plurality of the forms of the administration, for example, by a combination of oral and/or injection and/or topical application, etc.

In other cases the method of this invention is advantageously practiced by combining the administration forms in a time spaced sequence, for example, by using systemic application of one or more of the compositions for a time period and then applying one or more compositions topically, or by injection while continuing the systemic application, etc.

A preferred form of this invention comprises the concurrent administration to an afflicted human or animal of a composition comprising an admixture of active compounds selected from each of two groups, the amount from each group being in the range of about 0.1% to about 10% w/v. The first group of active compounds consists of compounds having the formula

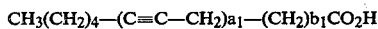

$$CH_3(CH_2)_4-(C\equiv C-CH_2)_{a_1}-(CH_2)_{b_1}CO_2H$$

wherein $a_1$ is 3 and 4 and $b_1$ is 5 when $a_1$ is 3 and $b_1$ is 2 when $a_1$ is 4.

The second group of active compounds consists of $PGE_1$, $PGE_2$, $PGE_3$, and the alkyl esters thereof containing from 1 to 8 carbon atoms inclusive, and 13,14-dihydro $PGE_1$ and the alkyl esters thereof containing from 1 to 8 carbon atoms inclusive.

A preferred range of active compounds from the above first group is about 0.01% to about 2% w/v and the preferred amount of compound from the above defined second group of active compounds is about 0.1% to about 5% w/v.

This composition is even further enhanced in its ability to alleviate psoriasis by the addition thereto of a glucocorticoid. The expression "glucocorticoid" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate for oral application or triamcinolone for topical therapy.

The amount of each of the materials from the first and second active groups of compounds in any particular composition may be varied over a wide range depending upon the severity of the psoriasis, the patient's reaction to drugs, and the degree of synergism which results from the particular combination of compounds in the composition. Use of one of the above specified combinations of active compounds enables the administration of a total amount of active compounds which is less than the amount of either of the active compounds when used alone in an otherwise smaller manner.

The following examples identify certain compositions which typify the amnner of combining selected active compounds with the pharmaceutical carrier in the use of the process of treatment of psoriasis as above generally described. They are not intended to represent the limitation of either the compositions, per se, or the process of this invention which is defined in the claim.

EXAMPLE 1

A soft-shell capsule was formulated from the following ingredients.

| Ingredients | Amount mg./capsule |
| --- | --- |
| Eicosatetrayn-(5,8,11,14)-oic-(1) acid (powder) | 262.5 |
| Neobee O[1] | 451.5 |
| Wax Mixture[2] | 10.0 |
| Lecithin, soy | 15.0 |

The soft-shell capsules were manufactured as follows:

The wax mixture was melted and slowly added to the Neobee O under constant stirring. After the melted wax mixture was added, the lecithin-soy was added to the mixture under constant stirring.

After all of the lecithin-soy was added eicosatetrayn-(5,8,11,14)-oic-(1) acid in powder form was added to the mix while stirring continuously with a high-speed stirrer. Mixing was continued until a uniform mixture was obtained. This mixture was then homogenized and de-aerated to obtain a suspension. This suspension was injected into the shell of a soft-shell gelatin capsule by means of a soft-shell capsule filling machine so as to form the capsule.

EXAMPLE 2 Oral Syrup

One thousand cc. of an aqueous suspension for oral use, containing in each 5 cc. dose 200 mg. of eicosatetrayn-(5,8,11,14)-oic-(1) acid is prepared from the following types and amounts of ingredients:

| Ingredients | Amount |
| --- | --- |
| Eicosatetrayn-(5,8,11,14)-oic-(1) acid | 40 gm. |
| Citric acid | 2 gm. |
| Benzoic acid | 1 gm. |
| Sucrose | 700 gm. |
| Tragacanth | 5 gm. |
| Lemon oil | 2 cc. |
| Deionized water q.s. | 1000 cc. |

The citric acid, benzoic acid, sucrose, tragacanth, and lemon oil are dispersed in sufficient water to make 850 cc. of solution, the eicosatetrayn-(5,8,11,14)-oic-(1) acid is stirred into the syrup until uniformly distributed. Sufficient water is added to make 1000 cc. 5 cc. doses three times per day may be used.

EXAMPLE 3 Parenteral Solution

A sterile aqueous solution for intramuscular use, containing in 1 cc. 50 mg. of eicosatetrayn-(5,8,11,14)-oic-(1) acid is prepared from the following types and amounts of materials:

| Ingredients | Amount |
| --- | --- |
| Eicosatetrayn-(5,8,11,14)-oic-(1) acid | 50 gm. |
| Lidocaine hydrochloride | 4 gm. |
| Methylparagen | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriasis at a dose of 1 cc. I.M. 4 times a day.

EXAMPLE 4 Topical Ointment

An ointment in the form of a homogenized and deaerated suspension was prepared by combining the following ingredients:

| Ingredient | Amount |
| --- | --- |
| Eicosatetrayn-(5,8,11,14)-oic-(1) acid (Powder) | 125 mg. |
| Neobee O | 215 mg. |
| Wax mixture | 4 mg. |
| Lecithin, soy | 6 mg. |

The above ointment was manufactured as follows:

The wax mixture was melted and slowly added to the Neobee O under constant stirring. After the melted wax mixture was added, the lecithin-soy was added to the mixture under constant sitrring.

After all of the lecithin-soy was added eicosatetrayn-(5,8,11,14)-oic-(1) acid in powder form was added to the mix while stirring continuously with a high-speed stirrer. Mixing was continued until a uniform mixture was obtained. This mixture was then homogenized and deaerated to obtain a suspension.

EXAMPLE 5

A suspension was prepared in homogenized and deaerated form by combining the following ingredients:

| Ingredient | Amount |
| --- | --- |
| Eicosatetrayn-(5,8,11,14)-oic-(1) acid | 75 mg. |
| PGE$_1$ | 85 mg. |
| Neobee O | 200 mg. |
| Wax mixture | 3.0 mg. |
| Lecithin, soy | 4.5 mg. |

The suspension was prepared by the following method:

The wax mixture was melted and slowly added to the Neobee O under constant stirring. After the melted was mixture was added, the lecithin-soy was added to the mixture under constant stirring.

After all of the lecithin-soy was added eicosatetrayn-(5,8,11,14)-oic-(1) acid in powder form and PGE$_1$ were added to the mix while stirring continuously with a high-speed stirrer. Mixing was continued until a uniform mixture was obtained. This mixture was then homogenized and deaerated to obtain a suspension.

EXAMPLE 6

A suspension was prepared in homogenized and deaerated form by combining the following ingredients:

| Ingredients | Amount |
| --- | --- |
| Eicosatetrayn-(5,8,11,14)-oic-(1) acid (Powder) | 75 mg. |
| PGE$_2$ | 85 mg. |
| Neobee O | 200 mg. |
| Wax Mixture | 3.0 mg. |
| Lecithin, soy | 4.5 mg. |

The suspension was prepared by the following method:

The wax mixture was melted and slowly added to the Neobee O under constant stirring. After the melted wax mixture was added, the lecithin-soy was added to the mixture under constant stirring.

After all of the lecithin-soy was added eicosatetrayn-(5,8,11,14)-oic-(1) acid in powder form and PGE$_2$ were added to the mix while stirring continuously with a high-speed stirrer. Mixing was continued until a uniform mixture was obtained. This mixture was then homogenized and deaerated to obtain a suspension.

EXAMPLE 7

A soft-shell capsule was formulated from the following ingredients.

| Ingredients | Amount mg./capsule |
| --- | --- |
| 5,8,11-eicosatriynoic acid | 262.5 |
| Neobee O | 451.5 |
| Wax Mixture | 10.0 |
| Lecithin, soy | 15.0 |

The soft-shell capsules were manufactured as follows:

The wax mixture was melted and slowly added to the Neobee O under constant stirring. After the melted wax mixture was added, the lecithin-soy was added to the mixture under constant stirring.

After all of the lecithin-soy was added, 5,8,11-eicosatriynoic acid in powder form was added to the mixture while stirring continuously with a high-speed stirring. Mixing was continued until a uniform mixture was obtained. This mixture was then homogenized and deaerated to obtain a suspension. This suspension was injected into the shell of a soft-shell gelatin capsule by means of a soft-shell capsule filling machine so as to form the capsule.

Three capsules, each containing about 200 milligrams of 5,8,11-eicosatriynoic acid, given three times per day, provides noticeable reduction in inflammation of psoriatic lesions, usually within one to two weeks of admission.

EXAMPLE 8 Topical Ointment

An ointment in the form of a homogenized and deaerated suspension was prepared by combining the following ingredients:

| Ingredient | Amount |
| --- | --- |
| 5,8,11-eicosatriynoic acid | 125 mg. |
| Neobee O | 215 mg. |
| Wax mixture | 4 mg. |
| Lecithin, soy | 6 mg. |

The above ointment was manufactured as follows:

The wax mixture was melted and slowly added to the Neobee O under constant stirring. After the melted was mixture was added, the lecithin-soy was added to the mixture under constant stirring.

After all of the lecithin-soy was added 5,8,11-eicosatriynoic acid in powder form was added to the mix while stirring continuously with a high-speed stirrer. Mixing was continued until a uniform mixture was obtained. This mixture was then homogenized and deaerated to obtain a suspension.

The above ointment, applied two to three times per day, with occlusive bandage, is effective to alleviate psoriasis.

We claim:

1. A method for treating psoriasis which comprises administering to the afflicted human or animal a composition containing as its active component at least one compound having the formula $$CH_3(CH_2)_4-(C\equiv C-CH_2)_{a_1}-(CH_2)_{b_1}CO_2H$$

wherein $a_1$ stands for an integer of from 3 to 5 and $b_1$ stands for an integer of form 0 to 8, and the alkyl esters of such compounds, said compound being in association with a pharmaceutical carrier, wherein said active component is present in an amount which is effective to alleviate psoriasis in the range of about 0.1% to about 15% w/v.

2. A method for treating psoriasis which comprises administering to the afflicted human or animal the composition containing as its active component at least one compound having the formula $$CH_3(CH_2)_4-(C\equiv C-CH_2)_{a_1}-(CH_2)_{b_1}CO_2H$$

wherein $a_1$ is 3 and 4 and $b_1$ is 5 when $a_1$ is 3 and $b_1$ is 2 when $a_1$ is 4, said compound being in association with a pharmaceutical carrier wherein said compound is present in an amount which is effective to alleviate psoriasis in the range of about 0.1% to about 15% w/v.

3. A method for treating psoriasis which comprises administering about 0.1 to about 5 gms. per day to the afflicted human or animal eicosatetrayn-(5,8,11,14)-oic-(1) acid in association with a pharmaceutical carrier, wherein said compound is present in an amount effective to alleviate psoriasis in the range of about 0.1% to about 15% w/v.

4. A method for treating psoriasis which comprises administering to the afflicted human or animal a composition containing as its active component at least one compound having the formula $$CH_3(CH_2)_m(C\equiv C-CH_2)_a(CH_2)_bCO_2H$$

and its alkyl esters wherein m is an integer from 5 to 9 inclusive, a is an integer of 2 to 5 and b is an integer of from 0 to 8, said compound being in association with a pharmaceutical carrier, wherein said active component is present in an amount which is effective to alleviate psoriasis in the range of about 0.1% to about 15% w/v.

5. A method for treating psoriasis which comprises administering about 0.1 to about 5 grams per day to the afflicted human or animal 5,8,11-eicosatriynoic acid in association with a pharmaceutical carrier, wherein said compound is present in an amount effective to alleviate psoriasis in the range of about 0.1% to about 15% w/v.

6. A method for treating psoriasis which comprises administering to the afflicted human or animal a composition containing as its active component at least one compound having the formula $$CH_3(CH_2)_m-(C\equiv C-CH_2)_a-(CH_2)_bCO_2H$$

wherein m stands for an integer from 5 to 9 inclusive, a stands for an integer of from 2 to 5 and b stands for an integer of from 0 to 8, and the alkyl esters of such compounds, and at least one compound from a second group of active compounds selected from the group consisting of $PGE_1$, $PGE_2$, $PGE_3$ and the alkyl esters thereof containing from 1 to 8 carbon atoms inclusive, and 13,14-dihydro $PGE_1$ and the alkyl esters thereof containing from 1 to 8 carbon atoms inclusive, said compounds being in association with a pharmaceutical carrier wherein the compound of said first group is present in an amount in the range of about 0.05% to about 2% and the compound selected from said second group is present in an amount of about 0.1% to about 15% w/v, the total thereof being effective to alleviate psoriasis.

7. The method in accordance with claim 6 wherein the compound from said first group is 5,8,11-eicosatriynoic acid.

8. The method in accordance with claim 6 wherein the compound from said second group of active compounds is $PGE_1$.

9. The method in accordance with claim 6 wherein the compound from said second group of active compounds is $PGE_2$.

10. The method in accordance with claim 7 wherein the compound from said second group is $PGE_1$.

11. The method in accordance with claim 7 wherein the compound from said second group is $PGE_2$.

* * * * *